United States Patent [19]

Grierson et al.

[11] Patent Number: 5,198,117
[45] Date of Patent: Mar. 30, 1993

[54] METHOD AND APPARATUS FOR PREPARING AN EPOXIDE BY ANIONIC DIALYSIS

[75] Inventors: Jeffery G. Grierson, Angleton; Dorothy L. Roerden, Lake Jackson, both of Tex.

[73] Assignee: The Dow Chemical Company, Midland, Mich.

[21] Appl. No.: 801,303

[22] Filed: Dec. 2, 1991

[51] Int. Cl.$^5$ .............................................. B01D 61/24
[52] U.S. Cl. ...................................... 210/638; 210/644
[58] Field of Search ................. 210/638, 644; 204/72, 204/299 R

[56] References Cited

U.S. PATENT DOCUMENTS

| | | | |
|---|---|---|---|
| 2,538,072 | 1/1951 | Zech | 260/348.6 |
| 3,335,156 | 8/1967 | Smith | 260/348.6 |
| 3,427,206 | 2/1969 | Wetherell | 136/146 |
| 3,454,490 | 7/1969 | Wallace | 210/22 |
| 3,556,965 | 1/1971 | D'Agostino et al. | 204/159.22 |
| 3,674,669 | 7/1972 | Tuwiner | 204/180 P |
| 3,723,264 | 3/1973 | Leduc | 204/80 |
| 4,012,303 | 3/1977 | D'Agostino et al. | 204/159.17 |
| 4,107,005 | 8/1978 | D'Agostino et al. | 204/98 |
| 4,113,922 | 9/1978 | D'Agostino et al. | 429/33 |
| 4,119,507 | 10/1978 | Simmrock et al. | 204/80 |
| 4,126,526 | 11/1978 | Kwon et al. | 204/98 |
| 4,230,549 | 10/1980 | D'Agostino et al. | 204/159.17 |
| 4,253,921 | 3/1981 | Baldwin et al. | 204/72 |
| 4,306,946 | 12/1981 | Kim | 204/51 |
| 4,339,473 | 7/1982 | D'Agostino et al. | 427/44 |
| 4,409,103 | 10/1983 | Cremonesi et al. | 210/638 |
| 4,414,090 | 11/1983 | D'Agostino et al. | 204/252 |
| 4,468,441 | 8/1984 | D'Agostino et al. | 429/105 |
| 4,543,169 | 9/1985 | D'Agostino et al. | 204/105 R |
| 4,559,144 | 12/1985 | Pfenninger et al. | 210/638 |
| 4,754,089 | 6/1988 | Matson et al. | 570/260 |
| 4,769,152 | 9/1988 | Igawa et al. | 210/638 |
| 4,786,597 | 11/1988 | Matson et al | 435/41 |
| 4,791,079 | 12/1988 | Hazbun | 502/4 |
| 4,800,162 | 1/1989 | Matson et al. | 435/280 |
| 4,827,071 | 5/1989 | Hazbun | 585/443 |

FOREIGN PATENT DOCUMENTS 63-4919 2/1988 Japan.
63-12148 3/1988 Japan.

OTHER PUBLICATIONS 60-197-665 (Abstract) Japan.
62-190,100 (Abstract) Japan.
88-20399 (Abstract) Australia.
266,059 (Abstract) EPA.
01-242,401 (Abstract) Japan.
Thomas A. Davies et al., *American Institute of Chemical Engineers Journal*, vol. 17, No. 4, pp. 1006-1008.
K. N. Mani, "Electrodialysis Water Splitting Technology", (pub. by Aquatech Systems of N.J.).
Raipore Products Catalog, (pub. by Rai Research Corp. of New York).

Primary Examiner—Frank Spear

[57] ABSTRACT

A process and apparatus for making a low salt epoxide is disclosed. The process comprises feeding a halohydrin solution into one compartment of a dialysis cell separated from a hydroxide dialyzing solution in a second compartment by an anionic membrane. An effective hydroxide concentration gradient across the membrane induces hydroxyl ion exchange for excess anions from the halohydrin solution so that electroneutrality across the membrane can be maintained.

20 Claims, 2 Drawing Sheets

METHOD AND APPARATUS FOR PREPARING AN EPOXIDE BY ANIONIC DIALYSIS

FIELD OF THE INVENTION

The present invention relates to a method for preparing an epoxide from a halohydrin by anionic dialysis. More particularly, the present invention relates to a method for producing a low salt epoxide wherein hydroxyl ions migrate to a reaction compartment across an anionic membrane in exchange for excess anions from the halohydrin solution.

BACKGROUND OF THE INVENTION

Epoxide compounds have a broad range of uses, particularly in the area of epoxy polymers. Quaternary ammonium epoxide salts (e.g. glycidyl ammonium salts) are commonly used for preparing cationically active cellulosic products such as starches, polyamines, and the like.

Epoxidation methods typically involve dehydrohalogenation of a halohydrin by addition of a base or direct synthesis by reaction with epichlorohydrin. Both methods, however, have drawbacks. Dehydrohalogenation generally results in the production of a mole equivalent of salt as a byproduct which is detrimental to the yield and end use of the epoxide. The presence of sodium chloride (NaCl), for example, can reverse the reaction because the chloride ion may nucleophilically react with the oxirane functionality, resulting in loss of product and lower yield. Waste disposal may become a problem where the salinity of the waste stream is subject to regulation. The use of epoxide solutions having a high chloride concentration is also limited in systems where chloride-based corrosion is a concern. On the other hand, direct synthesis requires use of a large molar excess of the epichlorohydrin, typically as solvent, which then has to be removed. Residual epichlorohydrin can also cause unwanted crosslinking in cellulosic applications.

Removing the salt from the epoxide product has been a major difficulty. One known method involves precipitation from an organic solvent, such as isopropyl alcohol, having miscibility with the epoxide followed by distillation recovery of the product. Large quantities of solvent are required, however, and many epoxides are heat sensitive so that the recovery process can significantly reduce the yield.

Consequently, efforts have been made to produce a low salt epoxide to obviate subsequent salt removal. U.S. Pat. No. 3,335,156 to Smith describes the use of anion exchange resins of the hydroxyl form. These resins are generally unsuitable for commercial scale production because the synthesis is mole-for-mole, thus requiring frequent regeneration of the resin.

Japanese Kokoku No. 63(1988)-4919 describes epoxidation of a halohydrin in an electrochemical cell wherein the salt byproduct is separated from the epoxide product by electrodialysis. A glycidyl ammonium salt is said to be prepared by electrodialysis of an ammonium halohydrin salt produced by a conventional method. The electrodialysis vessel comprises a series of adjacent chambers between a cathode and an anode separated by anionic exchange membranes. The apparatus also comprises alternating charges of either the halohydrin or a hydroxide solution. Anion migration is driven by an electric current into the adjacent chamber toward the anode. In this manner hydroxyl ions migrate into an adjacent halohydrin chamber and react to produce the epoxide, and halogen ions produced by the ring closure migrate toward the anode into the next adjacent hydroxide chamber. In such manner, ion impurities are said to be removed from the epoxide product.

In Japanese Kokoku No. 63(1988)-12148, a similar method is disclosed except that the electrodialysis vessel comprises a series of adjacent chambers between a cathode and anode separated by either anionic or cationic exchange membranes. Chambers charged with hydroxide and an electrolyte solution sandwich a chamber containing a charge of halohydrin. The chamber in the triplet containing the electrolyte solution is closest to the anode. Anionic exchange membranes separate the halohydrin chamber from adjacent chambers and a cationic exchange membrane separates the electrolyte chamber from the hydroxide chamber. When a direct current is imposed, a single direction migration of hydroxyl and halogen anions towards the anode occurs. In this manner, hydroxyl ions are said to migrate into the adjacent halohydrin chamber reacting with the halohydrin to produce the epoxide and halogen ions produced by the dehydrohalogenation reaction are said to migrate into the adjacent electrolyte chamber for removal as a metal salt. Metal ions are said to migrate oppositely (towards the cathode) from the hydroxide chamber through the cation membrane into the electrolyte solution for combination with the halogen ions above.

Use of an electrochemical cell for epoxidizing olefins is described in U.S. Pat. No. 3,723,364 to Leduc; U.S. Pat. No. 4,119,507 to Simmrock et al.; and U.S. Pat. No. 4,126,526 to Kwon et al. Generally, the olefin feed initially reacts with chlorine generated in an anode compartment to produce a chlorohydrin intermediate. Dehydrohalogenation is generally effected by base present in a cathode compartment.

Use of a membrane in an epoxidation process is described in Japanese Patent 60-197,665. A reverse osmosis membrane concentrates olefin halohydrins which are epoxidated by conventional techniques.

Various kinds of Donnan type dialysis processes are generally known in the art. Efficiency is generally the major shortcoming of such methods. Mass transfer must be adequate for the diffusing species; otherwise, the required time and membrane area become unreasonably great. Mass transfer rate for the product species must be low to avoid product losses into the dialysate.

Dialysis diffusion processes are described in several references including U.S. Pat. No. 3,454,490 to Wallace; U.S. Pat. No. 4,306,946 to Kim; and U.S. Pat. No. 4,559,144 to Pfenninger et al.; Japanese Patent 62-190,100; Thomas A. Davies et al., *American Institute of Chemical Engineers Journal*, Vol. 17, No. 4, Jul. 1971, pp. 1066–1008; and G. Wisniewska et al., *Desalination*, vol. 56, (1986) pp. 161–173.

Dialysis reaction processes are disclosed in Australian Patent 88-20399; U.S. Pat. No. 4,409,103 to Cremonesi et al.; and European Patent Application 266,059.

Catalytic membrane processes are disclosed in U.S. Pat. Nos. 4,786,597; 4,800,162 (and related PCT 88-07582); U.S. Pat. No. 4,754,089 (and related PCT 88-04286) all to Matson et al.; U.S. Pat. Nos. 4,791,079 and 4,827,071 to Hazbun; and Japanese patent 01-242,401.

An electrodialysis process is described in a paper by K. N. Mani, available from Aquatech Systems of New Jersey entitled "Electrodialysis Water Splitting Technology" wherein various anionic, cationic and bipolar membranes are disclosed to concentrate ions in solution and convert such ions into the acid or base. In this process, dialysis is driven by an electrical potential and water is split.

In the RAIPORE Products Catalog distributed by RAI Research Corp. of New York, dialysis is said to be useful in desalting applications, as reaction rate and pH controllers, for toxic anion or trace metal ion removal, as sensors, in bioreactors and in water treatment processes.

U.S. Pat. Nos. 4,543,169; 4,414,090; 4,230,549; 4,107,005; 3,674,669; 3,427,206; 4,468,441; 4,339,473; 4,113,922; 4,012,303; and 3,556,965 assigned to RAI Research Corp. disclose various aspects of the manufacture and use of dialysis membranes.

SUMMARY OF THE INVENTION

The present invention provides a process for efficiently producing a low salt epoxide by dehydrohalogenation of a halohydrin using anionic dialysis without application of an electric field. It has been discovered that the ratio of salt to product can be made very low by using a sufficiently low concentration of a hydroxide dialyzer. Furthermore, product losses are surprisingly light even for neutral charge halohydrin reactants having small molecular size.

In one embodiment, the present invention provides a method for producing an epoxide from a halohydrin, comprising the steps of: (a) feeding a halohydrin solution into a first compartment of a dialysis cell, wherein the solution in the first compartment is separated from a hydroxide dialyzing solution in a second compartment by an anionic membrane which inhibits halohydrin migration from the first to the second compartments; (b) inducing exchange of anions in the first compartment for hydroxyl anions in the second compartment by maintaining an effective hydroxide concentration differential between compartments, wherein the hydroxyl anions migrate to the first compartment, react with the halohydrin to produce anions as a byproduct and the byproduct anions migrate to the second compartment to maintain a neutral charge differential between the compartments; and (c) withdrawing epoxide dialysate solution from the first compartment having a low byproduct salt concentration. The halohydrin is preferably selected from the group consisting of:

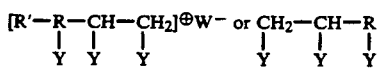

wherein R is a hydrocarbon lower alkyl radical having from 1 to about 5 carbon atoms; R' is an organic cation; W is an anion associated with the cation R'; and Y is independently selected from the group consisting of hydrogen, hydroxyl and X radicals comprising an electrophile leaving group selected from halogen, sulfate and phosphate radicals, but preferably halogen radicals, wherein at least one Y is a hydroxyl radical adjacent to at least one Y which is an X radical. Organic cationic radicals include onium and inium radicals such as ammonium, phosphonium, pyridinium, piperizinium, and the like. The halohydrin may also comprise a halohydrin polymer or polymer salt. In a preferred embodiment, the halohydrin comprises an ammonium halohydrin salt.

The exchange membrane preferably comprises a polymer film having a wet thickness between about 0.01 and 0.2 mm grafted with hydrophilic monomers selected from the group consisting of vinyl pyridine, styrene, vinyl acetate, acrylonitrile, acrylic acid and methacrylic acid, preferably converted to the cation form. The dialyzing solution comprises from about 0.01 to about 20 percent by weight, preferably from about 0.05 to about 10 percent by weight of an aqueous alkali metal hydroxide or ammonium hydroxide.

In another embodiment, the present invention comprises an apparatus for producing an epoxide from a halohydrin, comprising: (a) a dialysis cell having first and second compartments; (b) a charge of halohydrin feed solution in the first compartment; (c) a charge of hydroxide dialyzing solution in the second compartment; (d) an anionic membrane separating the compartments to inhibit halohydrin migration between the compartments; and (e) an effective hydroxide concentration differential between compartments to induce exchange of byproduct anions in the first compartment for hydroxyl anions in the second compartment, wherein the hydroxyl anions migrate to the first compartment, react with the halohydrin to produce anions as a byproduct and the byproduct anions migrate to the second compartment to maintain a neutral charge differential between the compartments.

DETAILED DESCRIPTION OF THE INVENTION

Figure 1:
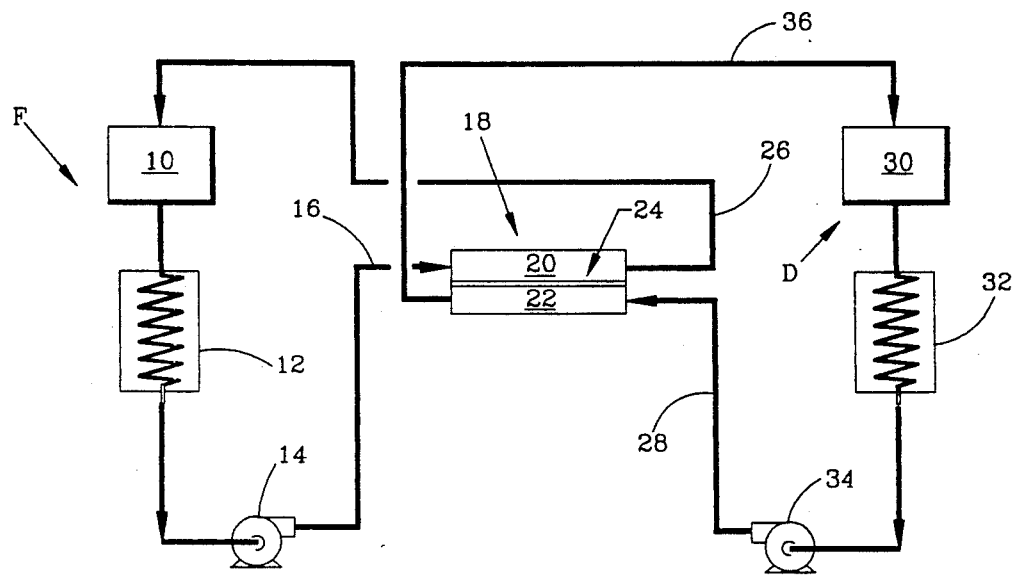
FIG. 1 is a schematic drawing of an embodiment of a dialysis process of the present invention. A feed recirculation system F comprises a feed tank 10, a temperature controlling exchanger 12 and a pump 14. A dialyzer recirculation system D comprises a dialyzer tank 30, a temperature controlling exchanger 32 and a pump 34. A feed stream 16 comprising an aqueous halohydrin solution is circulated through a feed compartment 20 of a dialysis cell 18, wherein the feed compartment 20 is separated from a dialyzer compartment 22 by an anionic dialysis membrane 24. An aqueous hydroxide dialyzing stream 28 is circulated through the dialyzer compartment 22, preferably countercurrent to the feed stream 16. A low salt epoxide product dialysate 26 exits the feed compartment 20. A hydroxide solution 36 having a higher concentration of byproduct halogen ions exits the dialyzer compartment 22. The hydroxide solution 36 has a relatively low concentration of the epoxide product.

The present invention provides a process and apparatus for producing a low salt epoxide by the dehydrohalogenation of a halohydrin. The invention overcomes problems associated with the prior art epoxides having excessive salt, especially chloride ion contamination. The invention is based on the discovery of a dialysis method for epoxidizing the halohydrin while concurrently substantially separating byproduct anions (mostly halogens), from the reaction effluent. The process is efficient and product losses are surprisingly low even when neutral charge small molecule halohydrin reactants are epoxidized.

As used herein, a "halohydrin" is an organic compound comprising a —CH(OH)CH(X)— moiety attached to a carbon, sulfur, nitrogen or phosphorus atom wherein X is an electrophilic leaving group preferably including a halogen, sulfate, phosphate, and the like radicals. Such compounds may be simple or polymeric molecules. Any simple halohydrin or polymeric halohydrin capable of forming an oxirane functionality with the loss of the electrophile X in the presence of hydroxyl ions and soluble in a polar solvent such as water, alcohol or any solvent system capable of solubilizing the base is suitable for use in the present invention.

Byproduct anions generally comprise X radicals released by the epoxidation reaction. In the case of a halohydrin salt (e.g. an ammonium salt), however, byproduct anions can comprise either X radicals or counterions of the ammonium salt.

Preferred simple halohydrins have the formulae:

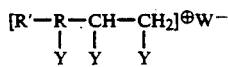   (I)

or

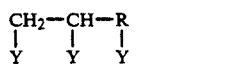   (II)

wherein R is a lower alkyl radical having from 1 to about 10 carbon atoms, preferably from 1 to about 5 carbon atoms; R' is an organic cation; W is an anion associated with the cation R'; and Y is independently selected from the group consisting of hydrogen, hydroxyl or X radicals wherein at least one Y is a hydroxyl radical adjacent to at least one Y which is an X radical. R may include methyl, ethyl, propyl, n-butyl, and the like. Suitable R' organic cations include one or more of onium and inium radicals such as ammonium, bis-ammonium, phosphonium, sulfonium, iodonium, and the like onium radicals and pyridinium, morpholinium, piperizinium, pyrolinium, and the like inium radicals. Ammonium cations are preferred. Examples of W include halogen ions.

Representative examples of quaternary ammonium halohydrin salts of formula (I) include 3-chloro-2-hydroxypropyltrimethylammonium chloride (quat), 1,3-dichloro-2-hydroxypropyltrimethylammonium chloride, 3-bromo-2-methyl-2-hydroxypropyltrimethylammonium chloride, 2-chloro-1,3-hydroxybutyl-trimethylammonium chloride, 3-chloro-2-hydroxypropyl-bis-trimethylammonium chloride and the like. Quat is a preferred halohydrin. Ammonium halohydrin salts are typically prepared by the aqueous addition of epichlorohydrin to a tertiary amine hydrohalide ($R_3NH^+Cl^-$). Alternatively, these compounds may be prepared by reacting amino compounds containing at least one tertiary amine group with an allyl halide, and then reacting the quaternized product with hypohalous acid to convert the allyl substituents to halohydrin moieties. Such preparatory techniques are well known in the art. Analogous onium halohydrin salts may be prepared by similar techniques. For example, a phosphonium halohydrin salt may be prepared by reacting a tertiary phosphine hydrohalide ($R_3PH^+Cl^-$) with an epihalohydrin, a sulfonium halohydrin salt may be prepared by reacting a sulfide hydrohalide ($R_2SH^+Cl^-$) with an epihalohydrin, and the like.

Representative examples of inium halohydrin salts of formula (I), are 3-chloro-2-hydroxypropylpyridinium chloride, N,N'-di(3-chloro-2-hydroxypropylmethyl)-piperizinium chloride, and the like. Inium salts may be prepared similarly to onium salts, e.g. by the aqueous addition of epichlorohydrin to the corresponding tertiary heterocyclic amine hydrohalide.

Representative examples of halohydrin compounds of formula (II) include 3-halo-1,2-dihydroxypropane, 1,3-dihalo-2-hydroxypropane, 2,3-dihalo-1-hydroxypropane, 1-halo-2-hydroxypropane, 2-halo-1-hydroxypropane, 2-halo-2-methyl-1-hydroxypropane, 2-halo-1-hydroxybutane, 2-halo-1-hydroxybutane, 2-halo-1,3-dihydroxybutane, 1-halo-2-methyl-2-hydroxybutane, and the like. Halohydrins may be isomer mixtures as is commonly known. For example propylene chlorohydrin (PCH) is typically an isomer mixture of about 15 percent by weight 2-chloro-1-hydroxypropane and 85 percent by weight 1-chloro-2-hydroxypropane. Such compounds may be prepared, for example by treating a corresponding unsaturated alcohol such as allyl alcohol with a hypohalous acid, or by other preparation techniques known in the art.

Soluble polymeric halohydrins are also suitable for use in the present invention. Such halohydrin polymers may be polymer salts. One preferred class of polymer salts are polymeric quaternary ammonium halohydrins. Such polymers are typically prepared by the condensation polymerization of a secondary amine and an epihalohydrin. Alternatively, a polyamine may be prepared by a free radical polymerization of a diallylamine hydrohalide salt, and then reacted with the epihalohydrin. Such preparatory techniques are well known in the art. Free halohydrin polymers may be prepared, for example, by polymerizing olefin and diolefin monomers so that unsaturation is present in the polymer backbone. The polymer may then be reacted with an epihalohydrin. Alternatively, polyhalohydrins may also be made from halohydrin monomers having polymerizable vinyl functionality.

The present invention also contemplates conducting a ring closing reaction on analogous halo-thiol compounds (wherein the hydroxy functionality on the halohydrin is a thiol functionality) which are soluble in the polar medium to produce analogous thiorane compounds.

In the practice of the present invention, Donnan dialysis is utilized to epoxidize the halohydrin and separate the byproduct anions produced from the reaction effluent. The epoxide may be represented as the product of the following reaction:

NaOH + —CH$_2$CH(OH)CH$_2$Cl ⟶

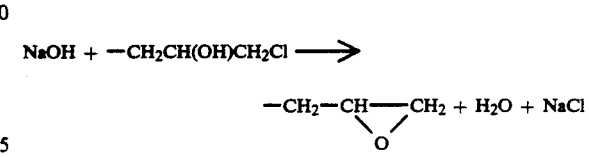

As a byproduct of the reaction, a mole of salt is produced.

The low salt epoxide made by the present invention has molar ratio of metal cation (e.g. Na+) to epoxide of less than about 0.25, preferably less than about 0.1, more preferably less than about 0.05, and most preferably less than about 0.02.

Donnan dialysis is based on the Donnan exclusion principle wherein the exclusion of one or more charged species by a membrane separating a pair of electrolytes and a concentration gradient of one of the electrolytes across the membrane drives an exchange of permeable ions having an opposite charge to the membrane. For charged membranes (e.g. anionic exchange membranes), like-charged ions (i.e. cations) are repelled by a membrane phase and charged ions opposite to that of the membrane (i.e. anions) which are permeable are exchanged in accordance with the principles of Donnan equilibria and conservation of charge. In the present invention, a feed halohydrin solution is in contact with one side of an anionic exchange membrane (i.e. having grafted cationic sites) and a hydroxide solution is in a dialyzing compartment in contact with an opposite side of the membrane. The hydroxyl anions migrate to the feed compartment and react with the halohydrin. Anions present in the reaction compartment, such as, for example, the electrophilic leaving group X produced by the reaction or the counter-ion W of a quaternary salt, migrate to the dialyzing compartment in exchange for the hydroxy ions so that charge neutrality may be maintained on both sides of the cell membrane. When a halohydrin salt is epoxidized, an excess anion concentration can occur upon release of the leaving group X.

In the present process, migration of product species and/or cation species such as sodium ions is undesirable and is substantially suppressed by the anionic membrane. Migration of sodium cations from the dialyzing compartment into the feed compartment would satisfy the electrical balance and reduce the separation efficiency for the anion species. Migration of product species from the feed compartment into the dialyzing compartment would reduce reaction yield.

Epoxide product diffusion is generally low, depending on the molecular size and the presence of a cationic charge on the molecule which is repulsed by similar charge sites on the membrane. Quaternary ammonium compounds such as 3-chloro-2-hydroxypropyltrimethylammonium chloride (quat) and polymeric quaternary salts (polyquats) have lower diffusion loss rates than non-ionic halohydrins having small molecular size such as PCH. However, even the diffusion loss rate of non-charged small molecular size halohydrins has been found to be relatively low.

Dialysis cells utilized in the present invention may have varying arrangements of compartments and membranes as is known in the art for bringing the base and feed solutions into the required membrane contact. One preferred configuration is a two-compartment cell separated by the anionic exchange membrane. In this type cell, the feed solution undergoing dialysis is circulated through one compartment and the base solution is circulated through the other. Multiple numbers of such cells may be combined in series or parallel groupings. Another suitable cell configuration is the shell-and-tube design. In this type cell, the anionic membrane comprises membrane tubes which are bundled together to provide a large surface area and compactness. The tube bundle is enclosed in the shell and the dialyzing solutions may flow either through the interior or around the exterior of the tubes according to practitioner preference. General aspects of shell and tube design are well known in the art. In the present process and apparatus, countercurrent flow is preferred for the dialyzing solutions. The only contact between fluids, in either configuration, is across opposing sides of the anionic membrane.

Selection of a suitable dialysis membrane permits efficient dialysis of the absorbent solution without the use of an electric potential to drive the diffusing species. The anionic exchange membranes used in the dialysis cell of the present process preferably comprise a polymeric substrate radiation grafted with a hydrophilic monomer suitable for providing strong cationic sites on the membrane surface. Hydrophilic refers to those monomers which are hydrophilic or can be made hydrophilic by subsequent treatment, such as quaternization, carboxylation, and the like. Examples of suitable substrate materials include polyethylene, polypropylene, polytetrafluoroethylene, polysesquifluoropropylene, ethylene-tetrafluoroethylene copolymer, fluorinated ethylene-propylene copolymer, and the like. For improved mechanical strength and oxidation, chemical and heat resistance, the polymer substrate may have varying degrees of crosslinking induced, for example, by irradiation.

Examples of hydrophilic monomers include vinyl pyridine, vinyl acetate, styrene, acrylonitrile, acrylic and methacrylic acid of which vinyl pyridine, acrylic and methacrylic acids are preferred.

The membrane may be further surface treated to convert the grafted functionality into cationic sites. For example, acrylic acid sites are converted to the corresponding alkali metal salt by treatment with dilute KOH, and pyridine sites are quaternized to the pyridinium salt by treatment with methyl bromide. Alternatively, the hydrophilic monomer may by converted to its cationic form before radiation grafting. In this manner, quaternized vinyl pyridinium methyl iodide may be grafted directly onto the polymer substrate.

Other treatments may be employed to enhance surface wettability and reduce diffusion resistance including washing with a cationic surface-active emulsifier such as quaternary ammonium salts, non-quaternary nitrogen bases, and the like. One such emulsifier is stearyldimethylbenzylammonium chloride sold by Rohm and Haas Co. under the trade name TRITON X 400.

The grafted polymeric base may be supported and laminated to a polymeric cloth, woven mesh, perforated sheet, and the like support member which provides greater mechanical strength. Other aspects of the description and manufacture of suitable anionic membranes may be found in U.S. Pat. Nos. 4,230,549 and 4,339,473 to D'Agostino et al. which are hereby incorporated herein by reference.

The anionic dialysis membrane of the present invention preferably has a wet thickness of from about 0.01 to about 0.2 mm.

Anionic exchange membranes found particularly responsive in the present invention include membranes sold under the trade designations RAIPORE R-1030 by RAI Research Corp. R-1030 is a thin tetrafluoroethylene-based polymer film of the strong anionic type having a wet thickness of about 0.05 mm.

The dialysis process of the present invention may be conducted as a batch or continuous operation depending on the preference of the practitioner. Design parameters such as membrane surface area and number of stages depend on the required production rate and purity (i.e. salt/product ratio) against the product loss rate.

For optimal operation of the dialysis reaction unit, pressure is preferably atmospheric to about 10 atmospheres and the cell operating temperature is preferably from about 5° C. to about 60° C. The temperature should not be so great as to structurally compromise the membrane. Atmospheric pressure to about 200 KPa gauge (30 psig) is conveniently employed for lower equipment and operating costs.

The feed solution generally comprises the halohydrin at a concentration of from about 0.1 to about 90 percent by weight. The dialyzing solution comprises a solution of alkali metal hydroxide, alkaline metal hydroxide, or ammonium hydroxide. When it is desired that the product concentration of metal ions (e.g. $Na^+$) be very low, ammonium hydroxide is a preferred dialyzer. Dialysis rates depend in part upon on hydroxide concentration which is typically maintained between about 0.01 to about 20 percent by weight of the solution, preferably between about 0.05 and about 10 percent by weight. If the hydroxide concentration is too low, the reaction rate will be undesirably low. On the other hand, if the hydroxide concentration is too great, the salt impurity concentration in the product may be too high. In addition, the operating life of the membrane may be impaired.

The following examples illustrate the use of the dialysis process of the present invention:

EXAMPLES 1-4

In the following examples, dialysis evaluations were performed on four different chlorohydrin solutions including 3-chloro-2-hydroxypropyltrimethylammonium chloride (quat, Example 1), propylene chlorohydrin (PCH, Example 2), 3-chloro-1,2-propanediol (Example 3) and 1,3-dichloro-2-hydroxypropane (Example 4). The tests were conducted in a dynamic countercurrent cell (see FIG. 1) utilizing from 1 to 3.5 wt % NaOH aqueous solution. Either two or three caustic stages were used.

The test equipment consisted of nearly identical closed loop recirculation systems entering opposite ends of adjacent chambers of the cell. The compartments were isolated by the membrane having opposing sides in continuous contact with the solution streams. Each recirculation system consisted of a tank feeding a pump. The pump inlet line was temperature controlled by a jacket heat exchanger and water bath. The dialysis cell comprised a shallow depth rectangular chamber longitudinally split into two plate-like flanged sections. The membrane comprised a RAIPORE R-1030 strong anionic membrane with a surface area of 0.026 $m^2$ (0.28 $ft^2$). The membrane was framed on its outer edges on both sides by VITON gaskets and was bolted between the cell halves. At opposite ends of each compartment were inlet and outlet connections for the feed and base streams so that flow through the cell would be countercurrent. The only contact between the two streams was diffusional transport across the membrane.

Initial samples were taken before charging the respective tanks. The feed tank was filled with 1000-1100 g of the chlorohydrin solution and the base solution tank was filled with 1000-1100 g of hydroxide solution before each run. The base and feed solutions were circulated at a pressure of about 14-20 kPa gauge (2-3 psig), at a controlled temperature of about 24° C. (75° F.) and a rate of about 1 liter/sec. The stages were simulated by running the reaction for a period of time, and then replacing the spent hydroxide solution with a fresh charge of the same weight as the initial charge. Halohydrin solution was not changed. Samples were again taken at the end of each stage until completion.

The feed solution was weighed at the beginning and end of the test and an approximate material balance was calculated to make a correction for osmotic water transport across the membrane. The samples were analyzed for chlorohydrins and epoxides by high performance liquid chromatography (HPLC) and sodium ion uptake by inductively coupled plasma atomic emission spectra (ICP). From the corrected concentration data, yield was calculated. This number represented percent conversion minus product losses into the base. The data appear in Table 1.

TABLE 1

| Example | Initial Conc. Feed (wt %) | Initial Conc. NaOH (wt %) | Stage | Contact Time (hr) | Yield (%) | Loss (%) | Conc. NaCl (ppm feed) |
|---|---|---|---|---|---|---|---|
| 1 | 16.18 | 3.5 | 1 | 4 | 58.9 | — | 350 |
|   |       |     | 2 | 4 | 99.5 | — | 1100 |
| 2 | 3.44 | 1 | 1 | 2 | 32.3 | 2.9 | — |
|   |       |   | 2 | 2 | 53.7 | 5.9 | — |
|   |       |   | 3 | 2 | 74.4 | 9.0 | 633 |
|   |       |   | 4[a] | 2[a] | >85[a] | <15[a] | — |
| 3 | 5.01 | 1 | 1 | 2 | 29.4 | — | — |
|   |       |   | 2 | 2 | 70.1 | — | — |
|   |       |   | 3 | 2 | 89.5 | — | — |
| 4 | 4.99 | 1.5 | 1 | 2 | 30.9 | — | — |
|   |       |     | 2 | 2 | 64.5 | — | — |
|   |       |     | 3 | 2 | 76.8 | — | — |

[a]hypothetical (extrapolation from the data)

Results in Table 1 indicate that the present invention gave excellent yields and residual salt concentrations for both halohydrin salts and non-ionic compounds. Losses into the base solution of the non-ionic halohydrins/propylene oxides (Examples 2-4) were surprisingly low in view of the thinness of the anionic exchange membrane and the small size of these non-charged molecules. This is a good measure of the barrier properties of the R-1030 membrane.

In Example 1, analysis of the $Na^+$ ions in the starting hydroxide solution was 19,721 ppm by ICP and 20,056 by titration (for $OH^-$) giving an average of 20,000 ppm. Sodium ion uptake was only 0.7% of the starting $Na^+$ concentration in the hydroxide solution for stage 1 and 1.5% for stage 2.

In Example 4, the epoxidation yield as determined by glycidol analysis of the final feed solution was 87.4% (compared to 76.8% by HPLC).

EXAMPLES 5-8

Four Donnan dialysis evaluations were performed on aqueous solutions of either 18 or 36 percent by weight of quat using two different hydroxide concentrations. The tests were conducted similarly to Examples 1-4 (see FIG. 1) using a similar dialysis cell and membrane. At the end of the evaluation period, epoxidation reaction rates and kinetics were determined and sodium uptake rates were calculated.

The feed tank was filled with 1200 g of the quat solution and the base solution tank was filled with 1200 g of hydroxide solution before each run. Solution temperatures were maintained at about 22° C. (72° F.) and solution pressure varied between 27.5 and 55 kPa gauge (4-8 psig). Two batch stages were simulated by running the reaction for 4 hours then replacing the spent hydroxide solution with a fresh charge using the same weight as the initial charge and conducting dialysis for an additional 4 hours. Halohydrin solution was not changed. Twenty gram samples were taken from each tank after 3 minutes of recirculation at 2.0 1/min. Additional 20 g samples were taken from each side at 80 minute intervals until completion.

Quat samples were analyzed for chlorohydrin and epoxide by HPLC and for Na+ by ICP. Hydroxide samples were also analyzed for Na+ by ICP. Water transport was determined by carefully measuring the amount of NaOH solution added and removed at each stage. Reported data were corrected for water transport.

Results are shown in Table 2. Example 5 had a conversion rate which was practically complete for the process conditions used. Essentially complete conversion for the other runs could be obtained given additional caustic stages.

TABLE 2

| Example | Composition | | Conversion (wt %) Time of dialysis (min) | | | | | | |
|---|---|---|---|---|---|---|---|---|---|
| | Quat (wt %) | NaOH (wt %) | 0 | 80 | 160 | 240 | 320 | 400 | 480 |
| 5 | 18 | 3.20 | 0.000 | 0.276 | 0.463 | 0.555 | 0.745 | 0.891 | 0.992 |
| 6 | 18 | 1.72 | 0.000 | — | 0.363 | 0.417 | 0.607 | 0.712 | 0.787 |
| 7 | 36 | 6.52 | 0.000 | 0.203 | 0.245 | 0.330 | 0.450 | 0.540 | 0.650 |
| 8 | 36 | 3.74 | 0.000 | 0.159 | 0.230 | 0.295 | 0.416 | — | 0.535 |

Figure 2:
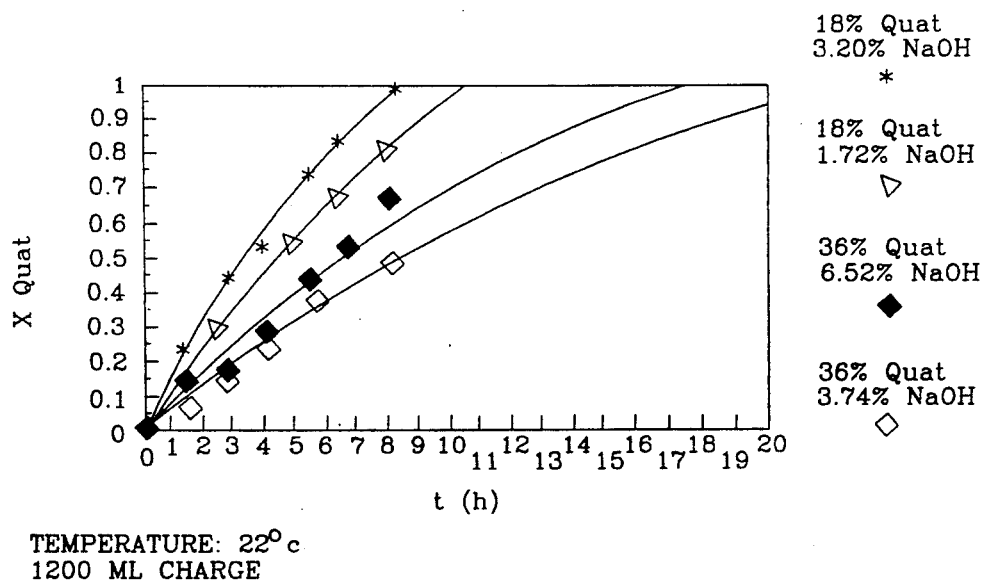
FIG. 2 shows a plot of the fractional conversion ($\chi$) of 3-chloro-2-hydroxypropyltrimethylammonium chloride (quat) to epoxide against time (t) for a starting concentration of 18 wt % quat using 1.72 ($\nabla$-$\nabla$-$\nabla$) and 3.20 (*-*-*) wt % NaOH and for 36 wt % quat using 3.74 ($\lozenge$-$\lozenge$-$\lozenge$) and 6.52 wt % ($\blacklozenge$, $\blacklozenge$, $\blacklozenge$) wt % NaOH.

The data in Table 2 which are also plotted in FIG. 2 show fractional conversion as a function of time. The curves (∇-∇-∇, 18 wt % quat/3.20 wt % NaOH; *-*-*, 18 wt % quat/1.72 wt % NaOH; ♦-♦-♦, 36 wt % quat/6.52 wt % NaOH; and ◊-◊-◊, 36 wt % quat/3 73 wt % NaOH) were found to conform to a power function of the following form:

$$\text{fractional conversion} = at^b \quad (I)$$

where t is time in hours, a and b are numerical constants and fractional conversion represents the fraction of chlorohydrin converted to epoxide. Regression parameters and coefficients of determination ($R^2$) are shown in Table 3.

TABLE 3

| Example | a | b | $R^2$ |
|---|---|---|---|
| 5 | 0.2234 | 0.7145 | 0.9926 |
| 6 | 0.1638 | 0.7587 | 0.9575 |
| 7 | 0.1473 | 0.6671 | 0.9402 |
| 8 | 0.1237 | 0.6899 | 0.9805 |

The $R^2$ values indicate a good data fit. In addition, the "a" parameters can be used to approximate initial conversion rates since they represent the fraction of quat converted into epoxide within the first hour of each run. These numbers also directly correlate to the initial OH fluxes presented in Table 4 given the assumption that the reaction of chlorohydrin with hydroxide is nearly instantaneous. These data show an increasing hydroxide flux as the NaOH concentration is increased in the Examples 5-8; however, the initial hydroxide flux does not double as the caustic concentration double which could be explained by a limiting hydroxide flux at higher caustic concentrations.

TABLE 4

| Example | OH conc. (wt %) | Initial OH$^-$ flux (mole/hr/ft$^2$) |
|---|---|---|
| 5 | 3.20 | 0.917 |
| 6 | 1.72 | 0.672 |
| 7 | 6.52 | 1.209 |
| 8 | 3.74 | 1.015 |

Sodium concentrations were monitored in the quat solution over the course of each run as a measure of product quality and to identify the important process optimization parameters for making a low salt epoxide. These results are presented in Table 5 and are plotted against run time in FIG. 3.

TABLE 5

| Example | Composition | | Na$^+$ Concentration (ppm) Time of dialysis (min) | | | | | | |
|---|---|---|---|---|---|---|---|---|---|
| | Quat (wt %) | NaOH (wt %) | 0 | 80 | 160 | 240 | 320 | 400 | 480 |
| 5 | 18 | 3.20 | 0 | 56 | 135 | 231 | 311 | 403 | 519 |
| 6 | 18 | 1.72 | 0 | 14 | 49 | 92 | 131 | 157 | 207 |
| 7 | 36 | 6.52 | 0 | 170 | 327 | 516 | 687 | 839 | 1037 |
| 8 | 36 | 3.74 | 0 | 72 | 146 | 225 | 306 | 386 | 473 |

Figure 3:
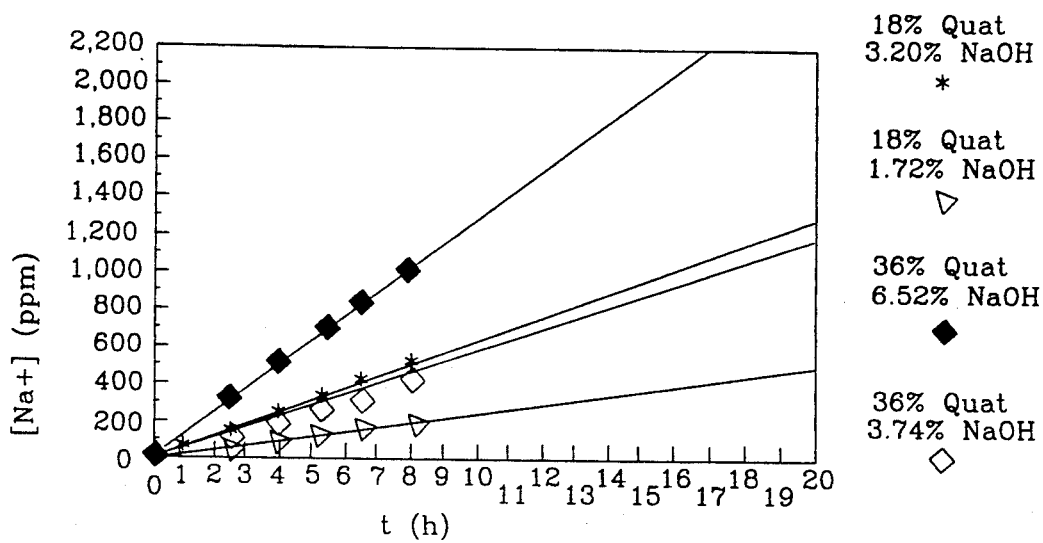
FIG. 3 shows a plot of weight percent sodium ion uptake [$Na^+$] in the product against time (t) for the epoxidation reactions of FIG. 2.

The curves (∇-∇-∇, 18 wt % quat/3.20 wt % NaOH; *-*-*, 18 wt % quat/1.72 wt % NaOH; ♦-♦-♦, 36 wt % quat/6.52 wt % NaOH; and ◊-◊-◊, 36 wt % quat/3.73 wt % NaOH) seen in FIG. 3 are straight lines as expected since sodium ion concentration changes relatively little on either side of the membrane and thereby results in a nearly constant driving force for sodium migration through the membrane. The data fit a zero order linear equation (y=mx+b) with $R^2$ greater than 0.987 and very small b values (≦23) in all four cases, indicating good fits. Since b≈0, y=mx (II) is a good approximation of sodium ion migration rate (moles/hr). From equations (I) and (II), total moles of Na+ in the epoxide product at 100% conversion can be estimated. Table 6 shows the slopes (m) for Examples 5–8 as well as time to completion, estimated Na+ concentration and ratio of Na+:epoxide (i.e. product quality) at complete conversion to epoxide.

TABLE 6

| Example | Feed Compositions Quat (wt %) | NaOH (wt %) | Na+ Migration (mole/hr) | Time to Completion (hr) | Na+ Conc. at Completion (moles) | Product Na+/Epoxide Ratio (molar) |
| --- | --- | --- | --- | --- | --- | --- |
| 5 | 18 | 3.20 | 0.003393 | 8.15 | 0.02766 | 0.0241 |
| 6 | 18 | 1.72 | 0.001384 | 10.85 | 0.01502 | 0.0131 |
| 7 | 36 | 6.52 | 0.006721 | 17.66 | 0.1187 | 0.0517 |
| 8 | 36 | 3.74 | 0.003981 | 20.68 | 0.06369 | 0.0277 |

Figure 4:
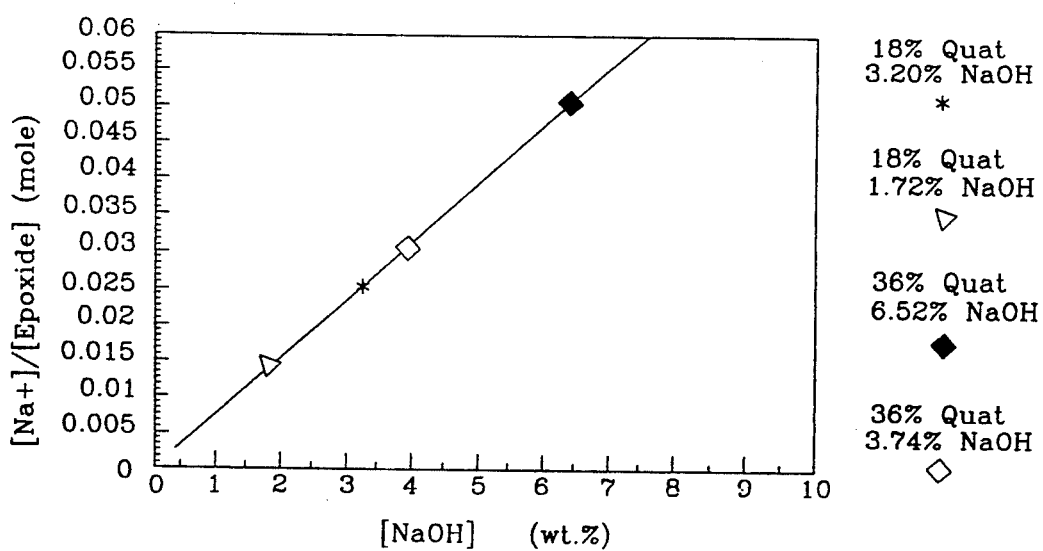
FIG. 4 shows a plot of predicted $Na^+$/epoxide mole ratio ([$Na^+$]/[epoxide]) against wt % NaOH ([NaOH]) for the epoxidation reactions of FIG. 2 at complete conversion to epoxide.

Operating conditions giving the lowest $Na^{30}$/epoxide mole ration are desirable. From Table 6, mole ratio of Na+ to epoxide is almost entirely dependent on caustic concentration. FIG. 4 (a plot of estimated Na+/epoxide mole ration at complete conversion vs. initial weight percent NaOH) shows the same caustic concentration dependency. Regression analysis of the data in FIG. 4 yields the relationship Na+/epoxide mole ratio$=0.007354[NaOH]^{1.028}$ with an $R^2=0.998$; wherein [NaOH] is the initial weight percent caustic concentration of the dialyzing solution. The tradeoff for minimizing salt concentration in the product is a need for greater membrane surface area and greater number of stages to obtain the same rate of epoxidation. However, as predicted, nearly any desired level of product purity can be achieved by use of sufficiently low base concentration.

The foregoing description of the invention is illustrative and explanatory thereof. Various changes in the materials, apparatus, and particular parts employed will occur to those skilled in the art. It is intended that all such variations within the scope and spirit of the appended claims be embraced thereby.

What is claimed is:

1. A method for producing an epoxide from a halohydrin, comprising the steps of:
   (a) feeding a halohydrin solution into a first compartment of a dialysis cell, wherein said solution in said first compartment is separated from a hydroxide dialyzing solution in a second compartment by an anionic membrane which inhibits halohydrin migration from said first to said second compartments;
   (b) inducing exchange of anions in said first compartment for hydroxyl anions in said second compartment by maintaining an effective hydroxide concentration differential between compartments, wherein said hydroxyl anions migrate to said first compartment, react with said halohydrin to produce byproduct anions and said byproduct anions migrate to said second compartment to maintain a neutral charge differential between said compartments; and
   (c) withdrawing epoxide dialysate solution from said first compartment having a low byproduct salt concentration.

2. The method of claim 1, wherein said halohydrin corresponds to one of the formulae:

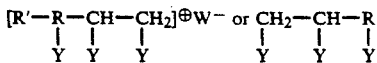

wherein R is a lower alkyl radical having from 1 to about 5 carbon atoms; R' is an organic cation; W is an anion associated with the cation R'; and Y is independently selected from the group consisting of hydrogen, hydroxyl and X radicals comprising an electrophile leaving group selected from halogen, sulfate and phosphate radicals, wherein at least one Y is a hydroxyl radical adjacent to at least one Y which is an X radical.

3. The method of claim 1, wherein said halohydrin comprises a halohydrin salt.

4. The method of claim wherein said halohydrin comprises a quaternary ammonium halohydrin salt.

5. The method of claim 1, wherein said halohydrin comprises a polymeric halohydrin.

6. The method of claim 1, wherein said halohydrin comprises a polymeric quaternary ammonium halohydrin salt.

7. The method of claim 1, wherein said halohydrin is selected from the group consisting of 3-halo-2-hydroxypropyltrimethylammonium halide, 2-halo-1-hydroxypropane, 1-halo-2-hydroxypropane, 3-halo-1,2-propanediol and 1,3-dihalo-2-hydroxypropane and mixtures thereof.

8. The method of claim 1, wherein said hydroxide solution has a concentration of from about 0.01 to about 20 percent by weight.

9. The method of claim 1, wherein said hydroxide solution has a concentration of from about 0.05 to about 10 percent by weight.

10. The method of claim 1, wherein said hydroxide solution is essentially free of halohydrin.

11. An apparatus for producing an epoxide from a halohydrin, comprising:
   (a) a dialysis cell having first and second compartments;
   (b) a charge of halohydrin feed solution in said first compartment;
   (c) a charge of hydroxide dialyzing solution in said second compartment;
   (d) an anionic membrane separating said compartments to inhibit halohydrin migration from said first compartment to said second compartment; and
   (e) an effective hydroxide concentration differential between compartments to induce exchange of anions in said first compartment for hydroxyl anion in said second compartment, wherein said hydroxyl anions migrate to said first compartment, react with said halohydrin to produce byproduct anions and said byproduct anions migrate to said second compartment to maintain a neutral charge differential between said compartments.

12. The apparatus of claim 11, wherein said halohydrin has one of the formulae:

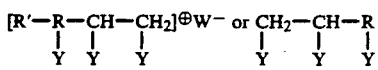

wherein R is a lower alkyl radical having from 1 to about 5 carbon atoms; R' is an organic cation; W is an anion associated with the cation R'; and Y is independently selected from the group consisting of hydrogen, hydroxyl and X radicals comprising an electrophile leaving group selected from halogen, sulfate and phosphate radicals, wherein at least one Y is a hydroxyl radical adjacent to at least one Y which is an X radical.

13. The apparatus of claim 11, wherein said halohydrin comprises a halohydrin salt.

14. The apparatus of claim 11, wherein said halohydrin comprises a quaternary ammonium halohydrin salt.

15. The apparatus of claim 11, wherein said halohydrin comprises a polymeric halohydrin.

16. The apparatus of claim 11, wherein said halohydrin comprises a polymeric quaternary ammonium halohydrin salt.

17. The apparatus of claim 11, wherein said halohydrin is selected from the group consisting of 3-halo-2-hydroxypropyltrimethylammonium halide, 2-halo-1-hydroxypropane, 1-halo-2-hydroxypropane, 3-halo-1,2-propanediol and 1,3-dihalo-2-hydroxypropane and mixtures thereof.

18. The apparatus of claim 11, wherein said hydroxide solution has a concentration of from about 0.01 to about 20 percent by weight.

19. The apparatus of claim 11, wherein said hydroxide solution has a concentration of from about 0.05 to about 10 percent by weight.

20. The apparatus of claim 11, wherein said hydroxide solution is essentially free of halohydrin.

* * * * *